US00PP24295P3

(12) United States Plant Patent
Radler

(10) Patent No.: US PP24,295 P3
(45) Date of Patent: Mar. 11, 2014

(54) CLIMBING ROSE PLANT NAMED 'RADCLEAN'

(50) Latin Name: *Rosa hybrida*
Varietal Denomination: Radclean

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 60 days.

(21) Appl. No.: 13/507,756

(22) Filed: Jul. 26, 2012

(65) Prior Publication Data

US 2014/0033375 P1 Jan. 30, 2014

(51) Int. Cl.
*A01H 5/00* (2006.01)

(52) U.S. Cl.
USPC ..... Plt./110

(58) Field of Classification Search
USPC ..... Plt./110
See application file for complete search history.

*Primary Examiner* — Annette Para
(74) *Attorney, Agent, or Firm* — Buchanan Ingersoll & Rooney PC

(57) ABSTRACT

A new and distinct variety of rose plant is provided which forms in abundance on a substantially continuous basis attractive double blossoms that are white when mature. The vegetation is vigorous and strong. The growth habit is upright and bushy with long canes that can be trained to climb. Attractive ornamental dark green foliage with a matte finish is formed. During observations to date the disease resistance has been found to be excellent, particularly with respect to Black Spot, Mildew, and Rust. The new variety is particularly well suited for growing as distinctive ornamentation in parks, gardens, and residential settings.

1 Drawing Sheet

Botanical/commercial classification: *Rosa hybrida*/Climbing Rose Plant.

Varietal denomination: cv. Radclean.

SUMMARY OF THE INVENTION

The new variety of *Rosa hybrida* shrub rose plant of the present invention was created in a cultivated area at Greenfield, Wis., U.S.A., by artificial pollination wherein a cross took place in the hope that it would yield the desired characteristics. The cross was carried out during 2005. The female parent (i.e., the seed parent) was the product of the cross of an Unnamed Variety (non-patented in the United States) with the 'Pretty Lady' variety (non-patented in the United States) as pollen parent. The 'Pretty Lady' variety sometimes is known as the 'SCRivo' variety. The male parent (i.e., the pollen parent) of the new variety was provided by open pollination and is of unknown origin. The parentage of the new variety can be summarized as follows:

(Unnamed Variety×'Pretty Lady')×Open Pollination.

The seeds resulting from the above pollination were sown and small plants were obtained which were physically and biologically different from each other. Selective study resulted in the identification of a single plant of the new variety.

It was found that the new climbing rose plant of the present invention possesses the following combination of characteristics:

(a) abundantly and substantially continuously forms attractive double blossoms that are white when mature,
(b) exhibits an upright and bushy growth habit with long canes that can be trained to climb,
(c) forms vigorous vegetation, (d) forms attractive ornamental dark green foliage with a matte finish, and
(e) exhibits excellent disease resistance.

Accordingly, the variety provides attractive double white blossoms combined with substantially continuous blooming, and resistance to common rose diseases, such as Black Spot, Mildew, and Rust.

The new variety well meets the needs of the horticultural industry. It can be grown to advantage as an attractive climber in parks, gardens, public areas, and in residential landscapes. The new variety is particularly well suited for providing attractive ornamentation in the landscape. The white blossom coloration contrasts nicely with the matte dark green foliage.

The new variety of the present invention can be readily distinguished from its 'Pretty Lady' ancestor, as well as other climbing rose varieties that are available to others for comparison, such as the 'Climbing Iceberg' variety (non-patented in the United States), the 'Dream White' variety (U.S. Plant patent application Ser. No. 11/101,346, filed Apr. 7, 2005—now abandoned), and the 'White Dawn' variety (non-patented in the United States). More specifically, the 'Pretty Lady' ancestor forms dissimilar semi-double light pink to cream blossoms. The blossoms of the 'Climbing Iceberg' variety are fragrant, unlike those of the new variety. The 'Dream White' variety also forms fragrant blossoms combined with dissimilar pink-tinged buds, and the 'White Dawn' variety forms blossoms having a substantially lesser number of petals (e.g., approximately 30 to 35 petals).

The characteristics of the new variety have been found at Wasco, Calif., U.S.A., to be homogeneous and stable and to be strictly transmissible by asexual propagation, such as the rooting of cuttings, from one generation to another. The new variety reproduces in a true-to-type manner by such asexual propagation.

The new variety has been named 'Radclean', and will be marketed under the CLOUD 10 trademark.

Brief Description of the Photograph

The accompanying photograph shows, as nearly true as it is reasonably possible to make the same in a color illustration of this character, typical specimens of the new variety. Mature flowering plants are shown at an age of approximately two years during June 2011 while growing outdoors at West Grove, Pa., U.S.A. The attractive blossoms, floral buds, and foliage are displayed.

DETAILED DESCRIPTION

The chart used in the identification of colors is that of The Royal Horticultural Society (R.H.S. Colour Chart—1995 or equivalent), London, England. The description is based on the observation of two-year-old specimens of the new variety during June while growing in greenhouses on their own roots at West Grove, Pa., U.S.A.

Class: Climbing Rose.

Plant:

*Height*.—Approximately 7 to 8 feet on average when mature.

*Width*.—Approximately 5 feet on average when mature.

*Habit*.—Upright and bushy with long canes that can be trained to climb.

Branches:

*Color*.—Young stems: commonly Green Group 143A. Adult wood: Greyed-Orange Group 177B overlaid with Greyed-Orange Group 177A.

*Texture*.—Young stems: smooth. Adult wood: somewhat rough to the touch.

*Thorns*.—Size: commonly approximately 8 to 12 mm on average. Quantity: abundant. Color on young stems: Yellow-Green Group 145A, and edged with Greyed-Purple Group 184B. Color on mature wood: Greyed-Green Group 197A.

Leaves:

*Leaflet number*.—3, 5, and 7.

*Leaflet texture*.—Generally smooth on both the upper and under surfaces.

*Leaf size*.—Approximately 9.5 cm in length on average, and approximately 7.5 cm in width on average for a five-leaflet leaf.

*Leaflet shape*.—Ovate, with somewhat acuminate apices, and rounded bases.

*Leaflet margins*.—Serrate.

*Leaflet size*.—Commonly approximately 45 mm in length on average and approximately 30 mm in width on average at the widest point for terminal leaflets, and approximately 35 mm in length on average and approximately 20 mm in width on average at the widest point for lower leaflets.

*Overall appearance*.—Abundant, and dark green with a matte finish.

*Color*.—Young leaves: upper surfaces commonly are Yellow-Green Group 144A edged with Greyed-Purple Group 184B, and under surfaces commonly are Yellow-Green Group 144B. Mature leaves: upper surfaces commonly are Green Group 139A, and under surfaces commonly are Green Group 137C.

Inflorescence:

*Bearing*.—Commonly one per stem or in clusters of approximately 2 to 5 blossoms per stem.

*Number*.—Often approximately 22 blossoms per plant at a given time.

*Peduncle*.—Length: commonly approximately 3.5 cm on average. Texture: generally smooth and commonly covered with short flexible thorns less than 1 mm in length. Color near Yellow-Green Group 144A.

*Sepals*.—Length: commonly approximately 22 mm on average. Width: commonly approximately 9 mm on average at the widest point. Number: five. Texture upper surface: commonly covered with short pubescence. Texture under surface: generally smooth. Color upper surface: Green Group 138B. Color under surface: Green Group 143A.

*Buds*.—Shape: commonly ovoid. Size: medium to small. Length: as the calyx breaks commonly approximately 15 mm on average. Diameter as the calyx breaks commonly approximately 12 mm on average at the widest point. Color (as the calyx breaks): commonly near Orange-White Group 159A.

*Flower*.—Form: fully double. Diameter: commonly approximately 6 cm on average when fully open. Color (when opening begins): upper surface: Yellow Group 7A blending to Yellow Group 8C with White Group 155C at the apex. Under surface: Yellow Group 10B blending to Yellow-White Group 158C at the apex. Color (at end of blooming): upper surface: White Group 155B. Under surface: White Group 155B. Petal number: commonly approximately 50 to 60 on average. Petal shape: narrowly obcordate commonly with a tendency to highly recurve. Petal margin: entire. Petal apex: obcordate. Petal base: cuneate. Petal size: commonly approximately 35 mm in length on average and approximately 27 mm in width on average. Fragrance: none noticeable. Petal drop: good, with the petals commonly dropping cleanly and freely. Accordingly, the blossoms commonly display an outstanding propensity to clean well at full maturity. Stamen number: commonly approximately 48 on average. Anthers: near Yellow-Orange Group 14D in coloration. Filaments: commonly approximately 5 mm in length and near White Group 155A in coloration. Pollen: commonly is near Yellow-Orange Group 14D in coloration. Pistils: commonly approximately 23 on average, separate and free. Styles: commonly approximately 4 mm in length on average, and the lower one-third commonly is Yellow-Green Group 144D with the remaining portion being near White Group 155A in coloration. Stigmas: commonly approximately 1 mm in size, and near Yellow Group 7C in coloration.

*Receptacle*.—Shape: generally spherical. Diameter: approximately 6 mm on average. Texture: smooth. Color: near Yellow-Green Group 144A in coloration.

Development:

*Vegetation*.—Vigorous and strong.

*Blossoming*.—Abundant and substantially continuous during the growing season.

*Resistance to diseases*.—Excellent, particularly with respect to Black Spot, Mildew, and Rust.

*Formation of hips/seeds*.—Sparse during observations to date.

The new 'Radclean' variety has not been observed under all possible environmental conditions to date. Accordingly, it is possible that the phenotypic expression may vary somewhat with changes in light intensity and duration, cultural practices, and other environmental conditions.

I claim:

1. A new and distinct climbing rose plant characterized by the following combination of characteristics:

(a) abundantly and substantially continuously forms attractive double blossoms that are white when mature, (b) exhibits an upright and bushy growth habit with long canes that can be trained to climb, (c) forms vigorous vegetation, (d) forms attractive ornamental dark green foliage with a matte finish, and (e) exhibits excellent disease resistance;

substantially as herein shown and described.

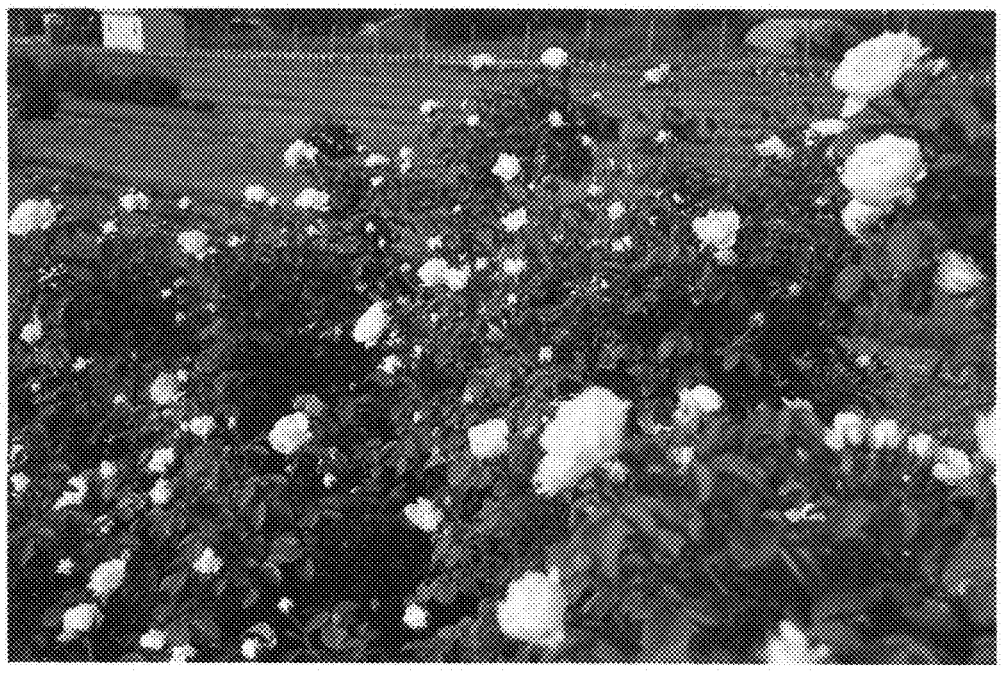

* * * * *